United States Patent [19]

Rombusch et al.

[11] Patent Number: 4,537,924

[45] Date of Patent: Aug. 27, 1985

[54] QUADRATIC ACID AMIDE DERIVATIVES, THEIR USE AS STABILIZERS, AND SYNTHETIC RESINS TREATED THEREWITH

[75] Inventors: Konrad Rombusch; Günther Maahs; Wolfgang Schäfer, all of Marl, Fed. Rep. of Germany

[73] Assignee: Chemische Werke Huels, AG, Marl, Fed. Rep. of Germany

[21] Appl. No.: 532,127

[22] Filed: Sep. 14, 1983

[30] Foreign Application Priority Data

Sep. 14, 1982 [DE] Fed. Rep. of Germany ....... 3233954

[51] Int. Cl.³ .............................................. C08K 5/34
[52] U.S. Cl. .................... 524/103; 546/186; 546/188; 546/189; 546/190
[58] Field of Search ................ 524/103; 546/186, 188, 546/189, 190

[56] References Cited

U.S. PATENT DOCUMENTS 4,170,588 10/1979 Hegenberg et al. ................ 524/242

FOREIGN PATENT DOCUMENTS 2634957 2/1980 Fed. Rep. of Germany .
2606026 3/1982 Fed. Rep. of Germany .
1531943 5/1968 France .
1186096 4/1970 United Kingdom .

OTHER PUBLICATIONS

Journal of Polymer Science; Polymer Chemistry ed., vol. 19, pp. 807–818.

Primary Examiner—John Kight
Assistant Examiner—Kriellion Morgan
Attorney, Agent, or Firm—Millen & White

[57] ABSTRACT

Quadratic acid bisamides and salts thereof having the formula I are effective stabilizers of synthetic resins, especially for imparting resistance to deterioration resulting from exposure to light

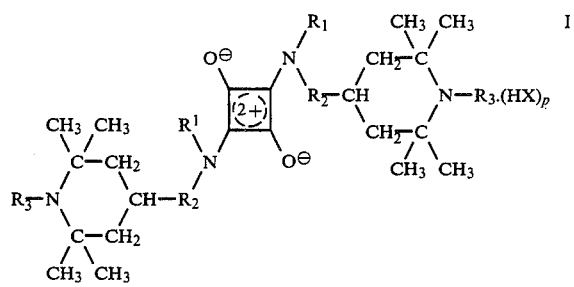

wherein $R_1$ is H, $C_{1-12}$ alkyl or OH-substituted $C_{2-12}$ alkyl;

$R_2$ is $-(CH_2)_m-O-_n$, wherein m is an integer of 2-6; n is 0 or 1;

$R_3$ is H, $CH_3$, $CH_2-CH_2-OH$, $CH_2-COOH$ or $CH_2-CH_2-COOH$;

HX is an acid equivalent of an unsubstituted or substituted monobasic, dibasic or polybasic organic acid of not more than 20 carbon atoms, or of sulfuric or phosphoric acid; and $0 \leq p \leq 2$.

20 Claims, No Drawings

QUADRATIC ACID AMIDE DERIVATIVES, THEIR USE AS STABILIZERS, AND SYNTHETIC RESINS TREATED THEREWITH

BACKGROUND OF THE INVENTION

The present invention relates to quadratic acid or squaric acid, see JACS 84, 2920 (1962), amide derivatives which are effective stabilizers for synthetic resins, and to synthetic resin compositions containing these stabilizers.

It is known that synthetic resins, under the effects of light and heat as well as under the influence of natural weathering, tend to yellow, to become brittle, and finally to disintegrate entirely. The resultant damage can reach considerable proportions. Therefore, it has been customary for some time to add a number of stabilizers to synthetic resins exposed to particularly deleterious environmental influences.

These stabilizers are compounds which have quite diverse chemical structures and which stabilize the synthetic resins against the effects of the natural environment by various mechanisms whose details are unknown in many cases. DOS 2,606,026 and DOS 2,634,957 disclose 1-oxa-4,8-diazaspiro[4,5]decanes which are added to polymers along with other customary stabilizers. The commercially available stabilizer designated TINUVIN 770 (see Comparative Example A) does not fulfill expectations with respect to its light-stabilizing effect.

The light-stabilizing effect of tetramethylpiperidine and its derivatives is due to their ability to efficiently scavenge radical intermediates formed in photooxidation processes, as disclosed in J. Polym. Sci. Polym. Chem. Ed., 19, 807 (1981).

DOS 2,638,855 discloses a quadratic acid amide substituted by a tetramethylpiperidine ring. The quadratic acid 1,3-bis-2′,2′,6′,6′-tetramethylpiperidon-(4′)-ide described therein not only differs structurally from the derivatives described herein, but furthermore, no commercially feasible syntheses for this compound are known. Certain quadratic acid 1,3-bisamides provided to be effective stabilizers in weathering tests due to their absorbing and quenching effects, as disclosed, e.g., in DOS 2,638,855.

However, all of the conventional stabilizers or stabilizer combinations have deficiencies which are especially evident in thin synthetic resin layers, viz.:

1. They are too volatile.
2. They can be easily extracted.
3. They exhibit a considerable tendency to migrate.

A need therefore continues to exist for stabilizers which do not show these disadvantages.

OBJECTS OF THE INVENTION

One object of this invention is to provide stabilizers for synthetic resins that provide effective protection against weathering, especially photooxidative deterioration.

Another object of the invention is to provide stabilizers for synthetic resins which are relatively nonvolatile, which are relatively stable to extraction and which do not show an appreciable tendency to migrate, particularly in thin resin layers.

A further object of the invention is to provide stabilized resin compositions, and molded articles produced therefrom, that resist weathering and maintain their appearance and good mechanical properties even under exposure to light and air.

Upon further study of the specification and appended claims, further objects and advantages of this invention will become apparent to those skilled in the art.

SUMMARY OF THE INVENTION

These and other objects can be attained by providing a quadratic acid amide or salt thereof having the formula

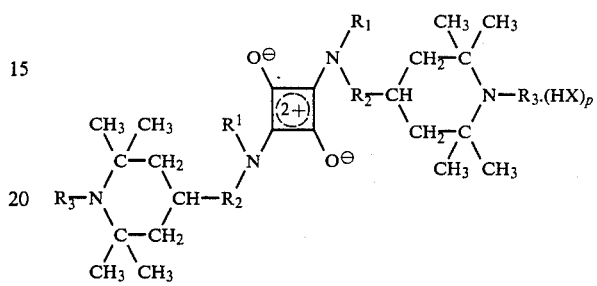

wherein $R_1$ is H, $C_{1-12}$ alkyl or OH-substituted $C_{2-12}$ alkyl;

$R_2$ is $+(CH_2)_m$—$O+_n$, wherein m is an integer of 2–6; n is 0 or 1, $R_3$ is H, $CH_3$, $CH_2$—$CH_2$—OH, $CH_2$—COOH or $CH_2$—$CH_2$—COOH;

HX is an acid equivalent of an unsubstituted or substituted monobasic, dibasic or polybasic organic acid of not more than 20 carbon atoms, or of sulfuric or phosphoric acid; and $0 \leq p \leq 2$.

DETAILED DISCUSSION

It has now been found, surprisingly, that the foregoing quadratic acid amides and salts thereof are effective as long-lasting stabilizers for synthetic resins.

Quadratic acid, or 1,2-dihydroxycyclobutenedione, reacts with amines to form the 1,3-bis(amino)cyclobutenediylium-2,4-diolates of the invention, having the resonance formulae Ia–c

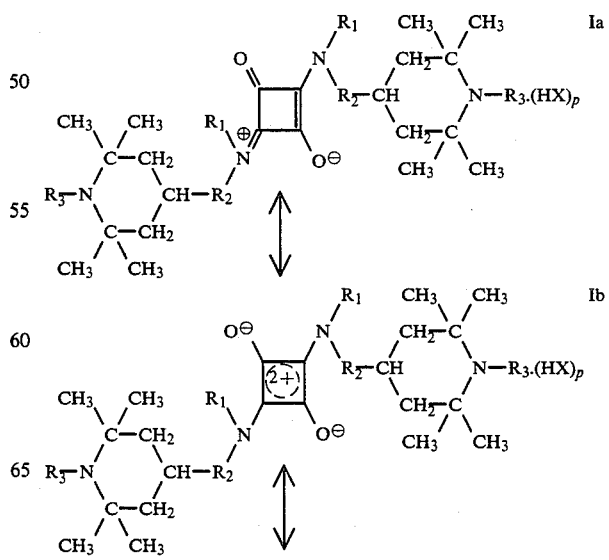

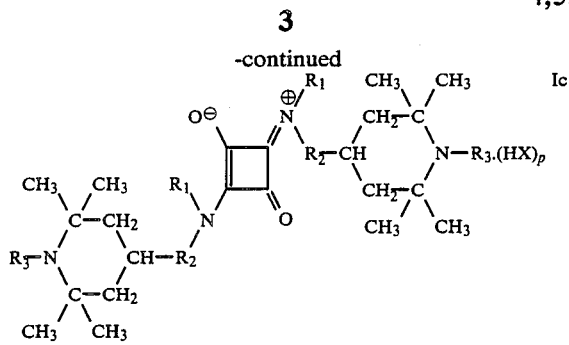

hereinafter represented with resonance form Ib alone, whereas 1,2-bis(amino)cyclobutenediylium-2,4-diolates are obtainable from the corresponding esters, the 1,2-alkoxycyclobutenediones (see DE-OS 16 18 211).

The stabilizers of the invention can be synthesized from tetramethylpiperidine derivatives of the formula

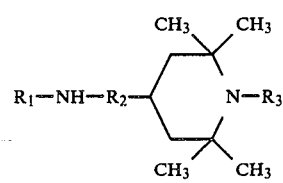

wherein $R_1$, $R_2$ and $R_3$ are as defined above.

$R_1$ can be H or any straight-chain or branched $C_{1-12}$ alkyl group, optionally substituted in any position other than $C_1$ by a hydroxy group, e.g., hydroxyethyl, propyl, isopropyl, n- or isobutyl, hexyl, decyl or dodecyl, and preferably H or $C_{3-8}$ alkyl.

As can be seen from the formula, the tetramethylpiperidine ring can be connected to the $R_1$-substituted amino group either directly through a valence bond, when n is 0, or through an oxyalkylene residue of 2 to 6 carbon atoms, such as, for example, an oxytrimethylene group or oxyhexamethylene group.

$R_3$ can be hydrogen, or a methyl, hydroxyethyl, carboxymethyl or carboxyethyl residue.

The aforementioned tetramethylpiperidine derivatives can be prepared by many conventional synthetic methods. If n equals 0, for example, the triacetonediamine obtainable according to DE-OS 30 03 843 is an important intermediate.

The tetramethylpiperidine derivates with $R_1=H$, $R_2=-(CH_2)_3-O-$ and $R_3=H$ can be obtained by the reaction of 4-hydroxy-2,2,6,6-tetramethylpiperidine with acrylonitrile and subsequent hydrogenation of the cyano group with raney-cobalt at 120° C. and 250 bar $H_2$ (see DE-OS 26 42 386).

The tetramethylpiperidine derivates with $R_1=H$, $R_2=-(CH_2)_6-O-$ and $R_3=H$ can be obtained by the reaction of 4-hydroxy-2,2,6,6-tetramethylpiperidine with 6-chlorcapronitrile and subsequent hydrogenation of the cyano group.

The tetramethylpiperidine derivates with $R_1=C_{1-12}$-alkyl or OH-substituted $C_{2-12}$-alkyl, $R_2=-$, $R_3=H$ can be either obtained by the reaction of triacetonediamine with aldehydes or ketones containing hydroxyl groups if necessary or the reaction of alkylamines with triacetoneamine (4-oxo-2,2,6,6-tetramethylpiperidine) at temperatures between 5° and 10° C. and subsequent catalytic hydrogenation with raney-nickel at 150° C. and 300 bar $H_2$.

The tetramethylpiperidine derivates with $R_1=$ hydroxyethyl; $R_2=-$, $R_3=H$ can be obtained by the reaction of one mole ethylene oxide with triacetonediamine at 90° C. in the presence of bortrifluoride and subsequent distillative separation from the bishydroxyethyl derivates.

The tetramethylpiperidine derivates with $R_1=H$, $R_2=-$ and $R_3=CH_2-COOH$ can be obtained by the reaction of triacetoneamine in the presence of chloracetic acid and subsequent hydrogenation with ammonia (see DE-OS 24 18 540).

As is described in example 8 the substituent $R_3$ can also be introduced in the quadratic acid amide.

The tetramethylpiperidine derivatives are reacted with quadratic acid at elevated temperature analogously to the process disclosed in DOS 2,638,855, corresponding to U.S. Pat. No. 4,170,588. If the process is carried out in the presence of a solvent, then the tetramethylpiperidine derivative is preferably utilized in the ratio of at least two moles per mole of quadratic acid. If the tetramethylpiperidine derivative is used as the solvent, then up to a 30-fold excess can be added. The reaction temperature preferably ranges between 100° and 250° C.

Salts of the quadratic acid bisamides can be subsequently prepared. For this purpose, a mixture of the quadratic acid bisamide and up to two equivalents of acid is heated at a temperature of at most 200° C. until the product is converted to a salt, as shown by IR spectrum (ammonium band 2400–3300 nm, carboxylate band at 1550 nm). The quadratic acid bisamide and the desired acid can also be reacted in a suitable solvent. After evaporation of the solvent the salts of the quadratic acid bisamide are obtained. Suitable solvents include ethers and alcohols with up to 8 carbon atoms, e.g. dimethyl ether, methyl tert.-butyl ether, methanol, ethanol etc. and dimethyl formamide.

Suitable as the acid component are monobasic organic acids of not more than 20 carbon atoms, e.g., acetic acid, lauric acid, stearic acid, and oleic acid, including sulfonic acids, e.g., dodecanesulfonic acid, as well as an acid equivalent of organic and inorganic dibasic and polybasic acids of not more than 20 carbon atoms, e.g., succinic acid, adipic acid, dodecane-1,12-dioic acid, phthalic acid, phosphoric acid, sulfuric acid, and phenylphosphonic acid. Also suitable are acids containing hydroxyl groups, e.g. citric acid, lactic acid, or aromatic or cycloaliphatic rings, e.g. benzoic acid and abietic acid.

In some cases the salts show a completely different solubility in the later mentioned synthetic resins compared with the bisamides. Thus, by varying p, the optimal stabilizing effect can easily be determined.

In most cases, the addition of the quadratic acid 1,3-bisamides as stabilizers will be adequate. In cases where an extremely low migration tendency is important, it is recommended that the salts be used.

Examples of specific compounds according to the invention are:

1,3-bis[N-n-propyl-N-(2,2,6,6-tetramethyl-4-piperidyl-)amino]cyclobutenediylium-2,4-diolate, 1,3-bis[N-n-octyl-N-(2,2,6,6-tetramethyl-4-piperidyl-)amino]cyclobutenediylium-2,4-diolate, 1,3-bis[N-n-octadecyl-N-(2,2,6,6-tetramethyl-4-piperidyl)amino]cyclobutenediylium-2,4-diolate, 1,3-bis[2,2,6,6-tetramethyl-4-piperidylaminopropylamino]cyclobutenediylium-2,4-diolate, 1,3-bis[1,2,2,6,6-pentamethyl-4-piperidylamino]cyclobutenediylium-2,4-diolate, 1,3-bis[(1-hydroxyethyl-2,2,6,6-tetramethyl-4-piperidyl)amino]cyclobutenediylium-2,4-diolate.

The following compounds are preferred:

1,3-bis[2,2,6,6-tetramethyl-4-piperidylamino]cyclobutenediylium-2,4-diolate and the salts thereof with an equivalent amount of dodecane-1,12-dioic acid and stearic acid, 1,3-bis[N-n-butyl-N-(2,2,6,6-tetramethyl-4-piperidyl)amino]cyclobutenediylium-2,4-diolate, 1,3-bis[N-isobutyl-N-(2,2,6,6-tetramethyl-4-piperidyl)amino]cyclobutenediylium-2,4-diolate, 1,3-bis[N-n-hexyl-N-(2,2,6,6-tetramethyl-4-piperidyl)amino]cyclobutenediylium-2,4-diolate, 1,3-bis[2,2,6,6-tetramethyl-4-piperidyloxypropylamino]cyclobutenediylium-2,4-diolate.

The stabilizers of the invention are preferably added to resins in amounts of 0.01–2% by weight, especially in amounts of 0.1–0.5% by weight, based on the synthetic resins.

Suitable synthetic resins include: homo- and copolymers of olefins or diolefins, e.g., polyisoprene, polybutene, polypropylene, polyethylene of low and high density, polybutadiene, saturated and unsaturated ethylene-propylene copolymers, ethylene-butene copolymers, ethylene-vinyl acetate copolymers butadiene-styrene copolymers and butadiene-styrene-acrylonitrile copolymers; homo- and copolymers of styrene and its homologs, e.g., polystyrene and styrene-butadiene copolymers; so-called high-impact strength types of polystyrene, such as graft polymers of styrene with elastomers, or mixtures of homo-, co- or graft polymers; homo-, co- or graft polymers of vinyl chloride, such as polyvinyl chloride, polyvinylidene chloride, vinyl chloride-vinylidene chloride copolymers, vinyl chloride-vinyl acetate copolymers; polyvinyl acetate; saturated and unsaturated polyesters, e.g., polyethylene terephthalate and polybutylene terephthalate; polyether esters; polyether ester amides; polyurethanes; polyisocyanurates; polyacrylonitrile and its copolymers; polycondensates, e.g., those based on acetophenone and formaldehyde; and the like.

Especially suitable are: polyamides, e.g., homopolyamides which can be conventionally produced from lactams of more than 5 ring carbon atoms, e.g., caprolactam, capryllactam, laurolactam, undecyllactam and enantholactam; and/or from the corresponding ω-amino acids; or from ω,ω'-diamines and ω,ω'-dicarboxylic acids of more than 3 carbon atoms between the functional groups; as well as the corresponding copolyamides. Examples of ω,ω'-diamines include, e.g., tetramethylenediamine, hexamethylenediamine, trimethylhexamethylenediamine, isophoronediamine, octamethylenediamine and dodecamethylenediamine. Suitable acids include, e.g., adipic acid, pimelic acid, suberic acid, azelaic acid, sebacic acid, undecanedioic acid, dodecanedioic acid, terephthalic acid and isophthalic acid.

The homo- and ciopolyamides of laurolactam are preferably utilized.

Use of the stabilizers of the invention in polyesters, polyether esters, polyether ester amides and polyurethanes is likewise advantageous. Examples include polymers based on terephthalic acid and 1,4-butanediol or a mixture of 1,4-butanediol and polytetrahydrofurane or a polymer based on 75% by weight of laurinlactam and 25% by weight of an equimolar mixture of dodecanedioic acid and polytetrehydrofuran.

The synthetic resins can contain, besides the stabilizers of this invention, further additives, such as pigments, colorants, plasticizers, or also—if desired—additional stabilizers, or optionally also blowing agents.

The stabilizers of this invention can be added to the synthetic resins by conventional techniques. For example, the bisamides can be added to the monomers prior to or during polymerization or polycondensation, or they can be incorporated into the molding compositions in kneaders or extrusion presses. However, it is also possible to add the stabilizers to solutions of the synthetic resins, from which powders are produced for, e.g., coating compounds or sheets, after removal of the solvent. The method of incorporation will depend, as usual, on the type of synthetic resin, its manufacture, or its processing.

Alternatively, the stabilizers can be introduced into the molding compositions during production of the molded articles. Where appropriate, they can be applied to the molded articles in a suitable way, e.g., by admixing it a pug mill or by spraying in the form of a solution. Thus, it is possible to utilize the stabilizers for synthetic resins serving for the manufacture of fibers, sheet stock, panels or other extruded or injection-molded shaped articles. The molded or unformed synthetic resins can also be utilized in the form of latices or for the production of foam materials.

The stabilizers of the invention find especially significant use in the production of molded articles which, even with long-term light exposure, particularly in the outside air, must not lose their good mechanical properties and, in conjunction therewith, their attractive appearance.

The production, physical properties, and utilization of several representatives of the bisamides will be described in greater detail in the following examples and tables.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

1,3-Bis[2,2,6,6-tetramethyl-4-piperidylamino]cyclobutenediylium-2,4-diolate

In an autoclave, 114.0 g of quadratic acid (1.0 mole), 390.8 g of 4-amino-2,2,6,6-tetramethylpiperidine (2.5 moles), and 800 cc of isopropanol were heated for five hours to 140° C. and then for 15 hours to 210° C. After cooling, the solid was suctioned off and dried. The thusobtained crude product was eluted three times with boiling methanol, washed with cold methanol, and then exhaustively dried, yielding as the remainder 353.1 g of white crystals (yield: 90.4%, mp>400° C., decomposition).

$C_{22}H_{38}N_4O_2$ (390.57): Calculated: C 67.65; H 9.81; N 14.34; O 8.19; Found: C 67.67; H 9.79; N 14.35; O 8.35

EXAMPLE 1.1

Lauric Acid Salt

A mixture of 390.6 g (1 mole) of 1,3-bis[2,2,6,6-tetramethyl-4-piperidylamino]cyclobutenediylium-2,4-diolate and 400 g (2 moles) of lauric acid was heated to 200° C. until the IR spectrum showed the product to be the quadratic acid salt.

EXAMPLE 1.2

Stearic Acid Salt

Prepared analogously to Example 1.1.

EXAMPLE 1.3

Benzoic Acid Salt

Produced in analogy to Example 1.1.

EXAMPLE 1.4

Abietic Acid Salt

Prepared analogously to Example 1.1.

EXAMPLE 1.5

Dodecane-1,12-dioic Acid Salt

Produced analogously to Example 1.1, using one mole of acid, corresponding to two acid equivalents.

EXAMPLE 2

1,3-Bis[N-n-propyl-N-(2,2,6,6-tetramethyl-4-piperidyl)amino]cyclobutenediylium-2,4-diolate Under agitation, 363.0 g (1.83 moles) of 4-n-propylamino-2,2,6,6-tetramethylpiperidine, 10.8 g (0.095 mole) of quadratic acid, and 150 cc of ethylhexanol were heated in a 1-liter agitated flask with attached water trap for five hours under reflux to boiling; the sump temperature was 205° C., and 3.0 cc of water was removed from the cycle. After concentration of the reaction solution, 33.9 g of crystals was precipitated. Yield: 75.2%, mp 198°–199° C. (from cyclohexane). Extinction (g/l.cm) at 278 nm: 27; at 335 nm: 95.

$C_{28}H_{50}O_2N_4$ (474.70): Calculated: C 70.84; H 10.62; N 11.80; O 6.74; Found: C 70.82; H 10.63; N 11.68; O 6.92

EXAMPLE 3

1,3-Bis[N-n-butyl-N-(2,2,6,6-tetramethyl-4-piperidyl)amino]cyclobutenediylium-2,4-diolate Under agitation, 392.9 g (1.85 moles) of 4-n-butylamino-2,2,6,6-tetramethylpiperidine, 10.0 g (0.0877 mole) of quadratic acid, and 150 cc of 2-ethylhexanol were heated to boiling under reflux in a 1-liter agitated flask with water trap; s temperature rose from 205° to 217° C., and 2.8 cc of water was removed from the cycle. The reaction solution was then distilled. The residue was boiled with petroleum ether. After cooling, vacuum-filtering, and drying, 38.9 g was obtained (88.2% yield), mp 151°–152° C. Extinction (g/l.cm) at 278 nm: 25; at 335 nm: 83.

$C_{30}H_{54}N_4O_2$ (502.79): Calculated: C 71.67; H 10.83; N 11.14; O 6.36; Found: C 71.35; H 10.88; N 11.01; O 6.56

EXAMPLE 4

1,3-Bis[N-isobutyl-N-(2,2,6,6-tetramethyl-4-piperidyl)amino]cyclobutenediylium-2,4-diolate In a 2-liter agitated flask with water trap attached thereto, 998.2 g (4.70 moles) of 4-isobutylamino-2,2,6,6-tetramethylpiperidine, 28.0 g (0.246 mole) of quadratic acid, and 400 cc of ethylhexanol were heated for 12 hours with stirring to boiling under reflux; after seven hours, the sump temperature reached the final value of 220° C., and 8.0 cc of water was removed from the cycle. 102.1 g of crystals precipitated from the reaction solution. Another 13.0 g was obtained from the distillation residue of the filtrate. Yield: 93.1%, mp 230°–232° C. (from methylcyclohexane). Extinction (g/l.cm) at 278 nm: 22; at 335 nm: 80.

$C_{30}H_{54}N_4O_2$ (502.79): Calculated: C 72.10; H 10.98; N 10.71; O 6.53; Found: C 71.67; H 10.83; N 11.14; O 6.36

EXAMPLE 5

1,3-Bis[N-n-hexyl-(2,2,6,6-tetramethyl-4-piperidyl)amino]cyclobutenediylium-2,4-diolate Under agitation, 1,155.2 g (4.75 moles) of 4-n-hexylamino-2,2,6,6-tetramethylpiperidine, 27.4 g (0.24 mole) of quadratic acid, and 250 cc of xylene were heated in a 2-liter agitated flask with water trap attached thereto for 2.5 hours under reflux to boiling; the solid matter was dissolved even before reaching the reflux above 150° C. The sump temperature was 202° C. The amount of water removed from the cycle was 8.0 cc. 113.7 g of product was obtained. Yield: 84.8% of theory, mp 152°–153° C. (from methylcyclohexane). Extinction (g/l.cm) at 328 nm: 76.

$C_{34}H_{62}O_2N_4$ (558.90): Calculated: 73.07; H 11.18; N 10.02; O 5.73; Found: 73.26; H 11.18; N 10.00; O 5.27

EXAMPLE 6

1,3-Bis[N-n-octyl-N-(2,2,6,6-tetramethyl-4-piperidyl)amino]cyclobutenediylium-2,4-diolate Under agitation, 339.6 g (1.26 moles) of 99.4% strength 4-n-octylamino-2,2,6,6-tetramethylpiperidine, 7.2 g (0.063 mole) of quadratic acid, and 150 cc of ethylhexanol was heated to boiling with reflux for 2.5 hours in a 1-liter stirred flask with water trap attached thereto; the solid matter was dissolved even before reaching reflux above 150° C. The sump temperature was 220° C. The amount of water removed from the cycle was 2.2 cc. Crystals precipitated from the reaction solution. After washing with petroleum ether and drying, 25.8 g was obtained. Yield: 84.4% of theory, mp 171°–175° C. (from cyclohexane). Extinction (g/l.cm) at 278 nm: 21; at 335 nm: 77.

$C_{38}H_{70}N_4O_2$ (615.01): Calculated: C 74.21; H 11.47; N 9.11; O 5.20; Found: C 74.30; H 11.58; N 8.98; O 4.96

EXAMPLE 7

1,3-Bis[N-2-hydroxyethyl-N-(2,2,6,6-tetramethyl-4-piperidyl)amino]cyclobutenediylium-2,4-diolate 5.7 g of quadratic acid (0.05 mole) and 50.1 g of 97.7% strength 4-(2-hydroxyethyl)amino-2,2,6,6-tetramethylpiperidine (0.244 mole) were heated for five hours to 200° C. After cooling, the reaction product was boiled with 150 cc of acetone and, after another cooling step, vacuum-filtered and washed with acetone, thus obtaining 16.0 g. Yield: 66.8% of theory, mp 309°–311° C. Extinction (g/l.cm) at 336 nm: 97.

$C_{26}H_{46}N_4O_4$ (478.68): Calculated: C 65.24; H 9.69; N 11.71; O 13.37; Found: C 65.05; H 9.72; N 11.70; O 13.46

EXAMPLE 8

1,3-Bis[1,2,2,6,6-pentamethyl-4-piperidylamino]cyclobutenediylium-2,4-diolate 58.6 g (0.15 mole) of 1,3-bis[2,2,6,6-tetramethyl-4-piperidylamino]cyclobutenediylium-2,4-diolate, 177.2 g of formalin (1.77 moles of $CH_2O$), and 55.8 g (1.2 moles) of 94% HCOOH were heated up, thus dissolving the solid phase. After heating the solution for seven hours under reflux to boiling, the solution was cooled, and the acidic solution was brought to pH 9 with sodium hydroxide solution, thus obtaining a precipitate which was washed with $H_2O$, producing 40.2 g (64.0% yield) of white crystals, mp > 340° C. (from cyclohexanol). Extinction (g/l.cm) (in DMF) at 324 nm: 64.

$C_{24}H_{42}N_4O_2$ (418.62): Calculated: C 68.86; H 10.11; N 13.38; O 7.64; Found: C 68.75; H 10.25; N 13.26; O 7.75

EXAMPLE 9

1,3-Bis[2,2,6,6-tetramethyl-4-piperidyloxypropylamino]cyclobutenediylium-2,4-diolate A slurry made up of 36.5 g (0.32 mole) of quadratic acid in 510.0 g (2.21 moles) of 94.9% strength 4-aminopropoxy-2,2,6,6-tetramethylpiperidine was heated for two hours to 160° C. and then for 1.5 hours to 180° C., removing 5.3 cc of water from the cycle and dissolving the solid phase. During cooling, the crude product was precipitated and was suctioned off, washed twice with hexane, and then dried, thus obtaining 154.4 g of crystals. Yield: 95.2% of theory, mp 218°–219° C. (from isopropanol). Extinction (g/l.cm) at 267 nm: 31; at 310 nm: 71.

$C_{28}H_{50}O_4N_4$ (506.74): Calculated C: C 66.37; H 9.95; N 11.06; O 12.63; Found: C 66.05; H 9.91; N 10.96; O 12.83

EXAMPLE 10

Synthetic Resins Treated with Quadratic Acid Bisamides (a) Polyamide 12 (Number Average Mol. Wt. 30,000: Producer: Chemische Werke Hüs AG, D-4370 Marl)

In a pug mill, polyamide 12 granules were combined with quadratic acid bisamides, and the resultant mixture was homogenized in a twin screw extruder. The granulated material obtained in this way was then molded into panels having a thickness of 1 mm, and chips of 30×10 mm were then cut therefrom.

(b) Polyether Esters (Number Average Mol. Wt. 25,000)

Into a polyether ester melt based on terephthalic acid, 1,4-butanediol, and polytetrahydrofuran, 0.5% by weight of the respective quadratic acid amide was introduced. After processing into granules, the latter were used to make press-molded panels of a thickness of 1 mm, from which chips were cut of 30×10 mm.

(c) Polypropylene (with a J Value of 330 and a Weight Average Molecular Weight of 380,000)

The stabilizer was thoroughly mixed with the polypropylene powder. The pulverulent mixture was homogenized in a screw extruder. The resultant granules were press-molded into panels.

(d) Polystyrene (with a Weight Average Molecular Weight of 260,000)

The procedure was effected as with polyamide 12 in Example 10(a).

(e) Acetophenone-Formaldehyde Resin

A mixture of 14 parts of a resin based on acetophenone and formaldehyde, 3 parts of plasticizer (adipic and phthalic acid esters), 83 parts of fillers (titanium dioxide and chalk), and 0.2 part of stabilizer was heated to melting and then cast into panels having a thickness of 3 mm.

COMPARATIVE EXAMPLE A

TINUVIN 770

This is sebacic acid di-4-hydroxy-2,2,6,6-tetramethylpiperidine ester, registered trademark of the company Ciba-Geigy, Basel, under the name of TINUVIN 770. The ester can be prepared according to DOS 1,929,921.

COMPARATIVE EXAMPLE B

HOSTAVIN

This compound is 2,2,4,4-tetramethyl-3,20-diaza-7-oxa-21-oxodispiro[5,1,11,2]heneicosane, registered under the name of HOSTAVIN as a trademark for Hoechst AG, Frankfurt. The compound is obtainable according to DOS 2,606,026.

COMPARATIVE EXAMPLE C 1,3-Bis(diethylamino)cyclobutenediylium-2,4-diolate

This compound was produced according to DOS 2,638,855.

COMPARATIVE EXAMPLE D 1,3-Bis(dibutylamino)cyclobutenediylium-2,4-diolate

This compound was prepared in accordance with DOS 2,638,855.

COMPARATIVE EXAMPLE E 1,3-Bis(cis-2,6-dimethylmorpholino)cyclobutenediylium-2,4-diolate This compound was produced by the method of DOS 2,638,855.

COMPARATIVE EXAMPLE F 1,3-Bis[(2-hydroxy-1-methylethyl)amino]cyclobutenediylium-2,4-diolate This compound was prepared according to DOS 2,638,855.

COMPARATIVE EXAMPLE G 1,3-Bispiperidinocyclobutenediylium-2,4-diolate

This compound was produced analogously to DOS 2,638,855.

COMPARATIVE EXAMPLE H

TINUVIN 120

This is a substituted benzoic acid phenyl ester of Ciba-Geigy, Basel.

COMPARATIVE EXAMPLE I

TINUVIN 622

This is an oligo ester of succinic acid and 1-hydroxyethyl-4-hydroxy-2,2,6,6-tetramethylpiperidine of Ciba-Geigy, Basel.

To test volatility, the quadratic acid bisamides or the synthetic resins treated therewith were subjected to thermogravimetric determination (cf. Tables 1 and 6). The heating-up rate was 10° C./min. A DuPont 950 Thermogravimetric Analyzer was applied.

The solubility values in water and dilute acetic acid (Tables 2 and 3), as well as the extraction values (Tables 4 and 7) confirm the low migrating tendency of the compounds according to the present invention.

The light exposure test was conducted with an apparatus equipped with ULTRA-VITALUX®-lamps*. The time period was measured by which the chips, bent by 180° in the direction of the nonirradiated side, showed breakage ("buckling test", Tables 5 and 9). Specimens of irradiated chips were dissolved in a mixture of 60% phenol and 40% 1,1,2,2-tetrachloroethane, and the change in viscosity based on concentration (J value) according to DIN 53 728 was chronologically tracked (Table 8).

*ULTRA-VITALUX®-lamps are quartz burners (300 Watt), whose light is filtered in such a way that it has a sun-like spectral distribution. Producer: Osram Finally, the chips, after irradiation, were subjected to optical testing for yellowing (Tables 10 and 11).

TABLE 1

Volatility of Pure Compound

| Stabilizer Disclosed in Example | Weight Drop of 2% | 50% | 80% |
|---|---|---|---|
| | at a Temperature (°C.) of: | | |
| 1 | 350 | 400 | 420 |
| 8 | 350 | 410 | 425 |
| 9 | 310 | 350 | 400 |
| A | 220 | 285 | 300 |
| B | 200 | 280 | 300 |
| C | 150 | 210 | 225 |
| D | 155 | 215 | 230 |
| E | 210 | 260 | 280 |

TABLE 2

Solubility of Pure Compound in Water

| Stabilizer Disclosed in Example | Solubility (g/100 g $H_2O$) at 22° C. | 100° C. |
|---|---|---|
| 1 | <0.002 | 0.015 |
| 3 | <0.01 | 0.08 |
| 4 | <0.01 | 0.07 |
| 5 | <0.01 | 0.03 |
| 6 | <0.01 | 0.02 |
| 9 | 0.24 | 0.95 |
| C | 240.2 | Not Determined |

TABLE 3

Solubility of Pure Compound in 10% Acetic Acid at 22° C.

| Stabilizer Disclosed in Example | Solubility (g/100 g 10% HAc) |
|---|---|
| 1.1 | 4.6 |
| 1.2 | 2.4 |
| 1.3 | 5.0 |
| 1.4 | <0.1 |
| 1.5 | 0.9 |
| A | 40.2 |

TABLE 3-continued

Solubility of Pure Compound in 10% Acetic Acid at 22° C.

| Stabilizer Disclosed in Example | Solubility (g/100 g 10% HAc) |
|---|---|
| F | 22.2 |

TABLE 4

Extraction of Stabilizers from Polyamide 12 with Boiling, Organic Solvents (cf. Example 10a)

| Stabilizer Disclosed in Example | Concentration of Stabilizer in Polyamide 12 (% by Weight) | Degree of Extraction after 8 Hour Treatment (% of Maximally Extractable Amount) in | |
|---|---|---|---|
| | | Methanol | Chloroform |
| 1 | 0.25 | 22.2 | 9.6 |
| A | 0.25 | 68.7 | 69.9 |
| B | 0.25 | 83.1 | 97.2 |

TABLE 5

Light Exposure Test with Stabilizers in Polyamide 12 (cf. Example 10a)

| Stabilizer Disclosed in Example | Concentration of Stabilizer in Polyamide 12 (% by Wt.) | Stabilizing Effect in Polyamide 12, Light Exposure (h) to Break | |
|---|---|---|---|
| | | Without Costabilizer | With Costabilizer(*) |
| 1 | 0.25 | 790 | 1,076 |
| 1.2 | 0.25(**) | 780 | 1,120 |
| 1.3 | 0.25(**) | 683 | 976 |
| 1.5 | 0.25(**) | 720 | 1,121 |
| 3 | 0.25 | 730 | 1,035 |
| 4 | 0.25 | 840 | 1,120 |
| 5 | 0.25 | 805 | 1,090 |
| 9 | 0.25 | 820 | 1,135 |
| C | 0.25 | 460 | 511 |
| E | 0.25 | 432 | 473 |
| G | 0.25 | 530 | 619 |

(*)The costabilizer employed was a mixture containing the following components-based on polyamide 12:
0.25% by weight of 2-(3,5-di-tert-butyl-2-hydroxyphenyl)-benzotriazole
0.25% by weight of N,N'—bis[3-(3,5-di-tert-butyl-4-hydroxyphenyl)propionyl]hexamethylenediamine
0.25% by weight of tris(2,4-di-tert-butylphenyl)phosphite.
(**)The value for the concentration refers to the quadratic acid bisamide on which the salt is based.

TABLE 6

Volatility of Stabilizers from Polyether Esters (*) (cf. Example 10b)

| Stabilizer Disclosed in Example | Degree of Sublimation after 24-Hour Treatment at 195° C. and 0.1 mbar (% of Maximally Sublimable Quantity) |
|---|---|
| 1 | 13 |
| 7 | 4 |
| A | 88 |

(*) As also in Tables 7 and 8, this is a polymer based on terephthalic acid, 1,4-butanediol, and polytetrahydrofuran with $M_n = 1,000$.

TABLE 7

Extraction of Stabilizers from Polyether Esters with Boiling, Organic Solvents (cf. Example 10b)

| Stabilizer Disclosed in Example | Degree of Extraction after 8-Hour Treatment (% of Maximally Extractable Quantity) in | |
|---|---|---|
| | Methanol (65° C.) | Toluene (110° C.) |
| 1 | 12 | 5 |
| 7 | 33 | 25 |
| A | 60 | 53 |

TABLE 8

Light Exposure Test with Stabilizers in Polyether Esters (cf. Example 10b)

| Stabilizer Disclosed in Example | Concentration of Stabilizer in Polyether Ester (% by Wt.) | Decrease in J-Value in % after | |
|---|---|---|---|
| | | 20 Days | 40 Days |
| 1 | 0.5 | 3 | 5 |
| 7 | 0.5 | 1 | 4 |
| A | 0.5 | 5 | 8 |
| G | 0.5 | 15 | 22 |

TABLE 9

Light Exposure Test with Stabilizers in Polypropylene (cf. Example 10c)

| Stabilizer Disclosed in Example | Concentration of Stabilizer in Polypropylene (% by Wt.) | Stabilizing Effect in Polypropylene, Light Exposure (h) to Break |
|---|---|---|
| 7 | 0.2 | 375 |
| A | 0.2 | 277 |
| G | 0.2 | 212 |

TABLE 10

Stabilizing Effect with Polystyrene (cf. Example 10d)

| Stabilizer Disclosed in Example | Concentration of Stabilizer in Polystyrene (% by Wt.) | Yellowness Index* after Irradiation Period of | |
|---|---|---|---|
| | | 750 Hrs. | 1230 Hrs. |
| 4 | 0.11 | 4.0 | 7.0 |
| 4 | 0.2 | 3.4 | 5.7 |
| 9 | 0.11 | 4.5 | 7.5 |
| E | 0.11 | 10.2 | 15.3 |
| H | 0.11 | 12.9 | 18.9 |

*This measurement was conducted with a Sun Test Device according to ASTMD 1925-70. Values of 0–7.5 correspond to a very low degree of yellowing; values of 10–20 correspond to a medium-strong degree, and values above 20 correspond to a strong degree of yellowing. For comparison: polystyrene without stabilizer content exhibits, after an irradiation period of 1,230 hours, a yellowness index of 22.1.

The polystyrene employed contained, in addition, 0.056% by weight of 2-(2-hydroxy-5-methyl)phenyl-2H-benzotriazole and 3.5% paraffin oil.

TABLE 11

Stabilizing Effect with an Acetophenone-Formaldehyde Resin (cf. Example 10e)

| Stabilizer Disclosed in Example | Concentration of Stabilizer in Resin (% by Wt.) | Degree of Yellowing after Irradiation Period of | |
|---|---|---|---|
| | | 84 Hrs. | 168 Hrs. |
| 4 | 0.2 | Very low | Low |
| 5 | 0.2 | Very low | Low |
| G | 0.2 | Medium | Strong |
| I | 0.2 | Medium | Strong |

These tests show that a wide variety of representative types of synthetic resins can be effectively stabilized by incorporation therein of suitable amounts of the quadratic acid bisamides of the invention, especially against deterioration resulting from exposure to light. Moreover, these advantages are surprisingly and unexpectedly superior for the stabilizers of the invention compared to a variety of commercially available prior art stabilizers.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A quadratic acid bisamide or salt thereof having the formula

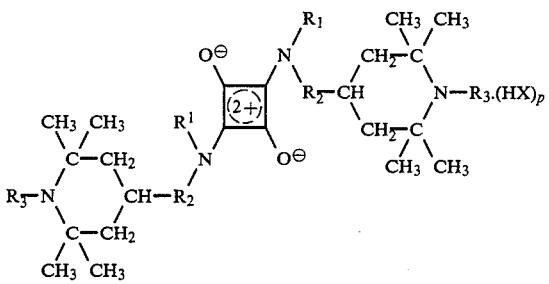

wherein $R_1$ is H, $C_{1-12}$ alkyl or OH-substituted $C_{2-12}$ alkyl;

$R_2$ is $+(CH_2)_m-O+_n$, wherein m is an integer of 2–6; n is 0 or 1;

$R_3$ is H, $CH_3$, $CH_2-CH_2-OH$, $CH_2-COOH$ or $CH_2-CH_2-COOH$;

HX is an acid equivalent of an unsubstituted or substituted monobasic, dibasic or polybasic organic acid of not more than 20 carbon atoms, or of sulfuric or phosphoric acid; and $0 \leq p \leq 2$.

2. A compound according to claim 1, wherein $R_1$ is $C_{3-8}$ alkyl; $R_2$ is a valence bond; $R_3$ is H; and p is 0.

3. A compound according to claim 1, wherein $R_1$ and $R_3$ are each H; and $R_2$ is a valence bond.

4. A compound according to claim 3, wherein p is 0.

5. A compound according to claim 3, wherein p is >0; and HX is an acid equivalent of dodecane-1,12-dioic acid or stearic acid.

6. 1,3-Bis[N-n-butyl-N-(2,2,6,6-tetramethyl-4-piperidyl)amino]cyclobutenediylium-2,4-diolate, a compound according to claim 1.

7. 1,3-Bis[N-isobutyl-N-(2,2,6,6-tetramethyl-4-piperidyl)amino]cyclobutenediylium-2,4-diolate, a compound according to claim 1.

8. 1,3-Bis[N-n-hexyl-N-(2,2,6,6-tetramethyl-4-piperidyl)amino]cyclobutenediylium-2,4-diolate, a compound according to claim 1.

9. 1,3-Bis[2,2,6,6-tetramethyl-4-piperidyloxypropylamino]cyclobutenediylium-2,4-diolate, a compound according to claim 1.

10. In a synthetic resin comprising an effective stabilizing amount of a stabilizer for imparting resistance to weathering, especially deterioration resulting from exposure to light, the improvement wherein said stabilizer is a quadratic acid bisamide or salt thereof having the formula

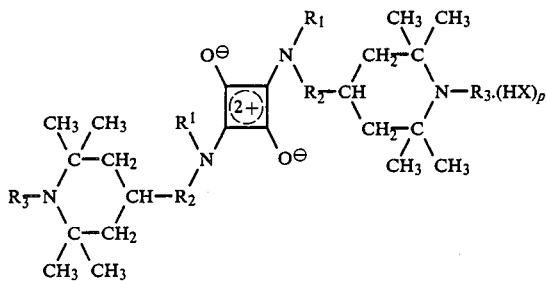

wherein $R_1$ is H, $C_{1-12}$ alkyl or OH-substituted $C_{2-12}$ alkyl;

$R_2$ is $+(CH_2)_m-O+_n$, wherein m is an integer of 2-6; n is 0 or 1;

$R_3$ is H, $CH_3$, $CH_2-CH_2-OH$, $CH_2-COOH$ or $CH_2-CH_2-COOH$;

HX is an acid equivalent of an unsubstituted or substituted monobasic, dibasic or polybasic organic acid of not more than 20 carbon atoms, or of sulfuric or phosphoric acid; and $0 \leq p \leq 2$.

11. A stabilized resin according to claim 10, wherein said effective stabilizing amount is 0.01–2% by weight, based on the weight of the resin.

12. A stabilized resin according to claim 11, which is a polyester, polyether ester, polyether ester amide or polyurethane.

13. A stabilized resin according to claim 11, which is a polyamide.

14. In a method of stabilizing a synthetic resin for imparting resistance to weathering, especially deterioration resulting from exposure to light, wherein an effective stabilizing amount of a stabilizer is incorporated in said resin, the improvement wherein said stabilizer is a quadratic acid bisamide or salt thereof having the formula

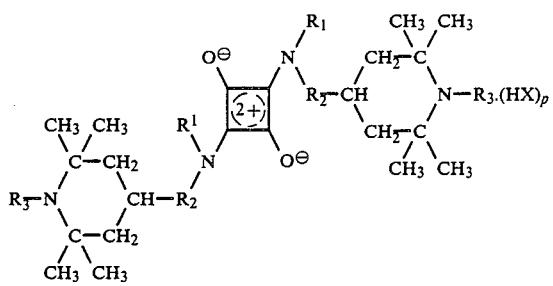

wherein $R_1$ is H, $C_{1-12}$ alkyl or OH-substituted $C_{2-12}$ alkyl;

$R_2$ is $+(CH_2)_m-O+_n$, wherein m is an integer of 2-6; n is 0 or 1;

$R_3$ is H, $CH_3$, $CH_2-CH_2-OH$, $CH_2-COOH$ or $CH_2-CH_2-COOH$;

HX is an acid equivalent of an unsubstituted or substituted monobasic, dibasic or polybasic organic acid of not more than 20 carbon atoms, or of sulfuric or phosphoric acid; and $0 \leq p \leq 2$.

15. A method according to claim 14, wherein said effective stabilizing amount is 0.01–2% by weight, based on the weight of the resin.

16. A method according to claim 14, wherein said resin is a polyester, polyether ester, polyether ester amide or polyurethane.

17. A method according to claim 14, wherein said resin is a polyamide.

18. A compound according to claim 1, wherein n is 1.

19. A stabilized resin according to claim 10, wherein n is 1.

20. A method according to claim 14, wherein n is 1.

* * * * *